United States Patent [19]

Cohen

[11] Patent Number: 4,619,795

[45] Date of Patent: Oct. 28, 1986

[54] METHOD FOR PREPARING LIPID VESICLES

[75] Inventor: Beri Cohen, White Plains, N.Y.

[73] Assignee: Technicon Instruments Corp., Tarrytown, N.Y.

[21] Appl. No.: 685,360

[22] Filed: Dec. 24, 1984

[51] Int. Cl.$^4$ .................... B01J 13/02; A61K 9/50
[52] U.S. Cl. ........................ 264/4.6; 424/1.1; 424/38; 428/402.2; 436/829
[58] Field of Search ............ 264/4.6; 428/402.2; 424/38, 1.1; 436/829

[56] References Cited

U.S. PATENT DOCUMENTS

| | | | |
|---|---|---|---|
| 4,186,183 | 1/1980 | Steck et al. | 428/402.2 X |
| 4,247,411 | 1/1981 | Vanlerberghe et al. | 264/4.6 |
| 4,280,816 | 7/1981 | Elahi | 422/57 X |
| 4,342,826 | 8/1982 | Cole | 436/829 X |
| 4,480,041 | 10/1984 | Myles et al. | 436/829 X |
| 4,485,054 | 11/1984 | Mezei et al. | 264/4.6 |

Primary Examiner—Richard D. Lovering
Attorney, Agent, or Firm—S. P. Tedesco; E. B. Lipscomb, III

[57] ABSTRACT

A method for forming vesicles is described, wherein a lipid coating is formed onto a deformable surface. During hydration, the lipid coating is fragmented by deformation of the surface. The resulting fragments of the lipid coating are dispersed in the hydrating medium, so as to be subjected to multidirectional hydration, whereby formation of vesicles is accelerated. In the preferred embodiment, such surface is defined by a plurality of water-swellable particles formed of a polymeric material.

15 Claims, No Drawings

METHOD FOR PREPARING LIPID VESICLES

BACKGROUND OF THE INVENTION

1. Field of the Invention

The present invention relates generally to the preparation of lipid vesicles, or liposomes, and particularly to the preparation of such vesicles having components, which may be membrane-incorporated or encapsulated, to render such vesicles suitable for therapeutic or diagnostic applications.

2. Brief Description of the Prior Art

Lipid vesicles, whether single- or multi-compartmented, have walls composed of lipids, particularly lipid mixtures including at least one phospholipid, in the form of continuous membranes. For a general view of the preparation, properties and uses of lipid vesicles, reference is made to Papahadjopoulos et al., (Eds.), Liposomes, Ann. N.Y. Acad. Sci., Vol. 308 (1978); Tom et al (Eds.), *Liposomes and Immunobiology,* Elsevier North Holland Inc., N.Y. (1980); Gregoriadis et al, (Eds.) *Liposomes in Biological Systems,* John Wiley & Sons, N.Y. (1980); Knight (Ed.), *Liposomes: From Physical Structure to Therapeutic Applications,* Elsevier North Holland Inc., N.Y. (1981); and Gregoriadis (Ed.), *Liposome Technology,* Vol. 1, CRC Press, Boca Raton, Fla. (1984). As discussed in these references, vesicles have been prepared in the past by numerous methods, each of which has certain advantages and disadvantages.

The earliest of these methods employs a film-formation techniques which involves the preparation of multilamellar vesicles (MLVs) by depositing the membrane components, dissolved in suitable organic solvents, as a coating film on the internal wall of a glass vessel, e.g., by evaporation. An aqueous solution of the materials to be encapsulated is introduced into the vessel as a hydrating mixture. The vessel is shaken or rotated for a period of time, to peel individual layers of the lipid coating to form vesicles which encapsulate or entrap the hydration mixture. The size of the resulting vesicles can vary from a fraction of a micron to several microns. Long hydration periods (10-20 hours) are normally required for satisfactory entrapment. The degree of entrapment depends upon such physical and mechanical factors as the nature of the surface upon which the lipid coating is deposited, the manner of agitation, the thickness of the deposited coating, etc. Also, the resulting vesicles can vary widely in size, for example, ranging between 0.1 microns to several microns. As the number of lipid vesicles produced is a function of the effective surface of the vessel, scale-up to achieve production-size quantities of lipid vesicles by this method would require very large vessels.

Alternatively, small unilamellar vesicles (SUVs) have been prepared by sonication of lipid mixtures or MLVs prepared by the film-formation technique described above. Typical sizes of SUVs are usually in the range of 20-100 nm and the size distribution is usually narrower than for the MVLs. While SUVs are useful for encapsulating materials of low molecular weights, e.g., drugs, they are too small to efficiently encapsulate proteins such as enzymes or antibodies, nucleic acids and other high molecular weight polymers. For that purpose, the SUVs can be enlarged to form large unilamellar vesicles (LUVs) by a series of freezing and thawing cycles in the hydrating medium and in the presence of alkali metal ions. This method is even more time-consuming than the film-formation technique described above, in that the additional steps of sonication and freezing and thawing are required.

Another method for forming vesicles employs a reverse-phase evaporation technique. In this method, lipids are dissolved in an appropriate organic solvent or solvent mixture having the same density as the hydrating mixture. The lipid solution is intimately dispersed in the hydrating mixture by sonication or vigorous shaking leading to formation of an emulsion. The organic solvent is subsequently evaporated to a level whereat reverse micelles are formed. Further evaporation and shaking of the remaining solution results in the formation of LUVs. The disadvantages of this method are the technical difficulty associated with the emulsification process and the risk of denaturing sensitive molecules, such as proteins and nucleic acids, during the emulsification process due to their prolonged contact with organic solvents.

Also, in infusion method, which is similar to the reverse-phase evaporation technique, has been employed, whereby lipids are initially dissolved in an organic solvent, e.g., ether, ethanol, etc. The resulting solution is injected as a tiny stream into the warm hydrating mixture, to allow the solvent to dissolve or evaporate. As a result, lipids are dispersed in the hydrating mixture and form vesicles. Vesicles formed either by ethanol or ether infusion are relatively small (0.4 microns or less) and unsuitable for applications requiring a large ratio of entrapped volume to membrane surface, e.g., immunodiagnostics. Vesicles formed by ethanol infusion exhibit relatively poor encapsulation efficiency as compared to those produced by ether infusion. Vacuum or heat may be applied to accelerate solvent evaporation. The danger does exist, however, that sensitive molecules may be denatured by the heat or by contact with the organic solvent.

A further method employs a detergent-removal technique. In such method, lipids are introduced into an aqueous medium containing a detergent, which solubilizes them. The detergent is subsequently removed by exhaustive dialysis whereupon the lipids become insoluble in the agueous medium and tend to form vesicles. Long dialysis times are required to completely remove the detergent. Even very small amounts of detergent remaining in the medium will affect the ultimate permeability of the vesicle and, hence, its usefulness as a diagnostic or therapeutic reagent.

When considering a method for the commercial production of vesicles for therapeutic or diagnostic applications, many requirements exist. The method of choice should be fast, easy to scale-up for production quantities, and maximize the encapsulation or entrapment of solutes present in the hydrating mixture within the vesicle. Also, the method should not adversely affect the chemical stability of the components involved in the vesicle formation process.

The prior art methods, described above, each suffers from one or more disadvantages. Usually, the combined time for preparation and purification of the vesicles is of the order of many hours. For scale-up purposes, a method that depends on liposome formation at the surface of a container, such as in the film-formation technique or the detergent removal technique, is likely to be difficult to scale-up. The surface area of a spherical container increases as the square of the diameter, whereas the volume increases as the cube of such diameter. Eventually, large and cumbersome apparatus would be required for commercial production. Several of the methods mentioned above result in the production of vesicles having small size and poor encapsulation efficiency. Methods of vesicle formation in which conditions, such as contact with organic solvents, emulsification, heat, etc., that may cause denaturation of biological molecules are not preferred.

SUMMARY OF THE INVENTION

In contrast to the shortcomings of the various prior art methods discussed above, the method of the present invention considerably simplifies the preparation of vesicles, is readily adaptable to scale-up for commercial production and avoids the possibility of proteins or other sensitive molecules being denatured during the hydrating process.

The present invention contemplates initially forming a coating or film of lipid on a substrate surface which is deformable. In the preferred method, such surface is defined by a particle which is water-swellable, so as to increase in size when exposed to an aqueous hydrating medium, whereby its surface is deformed. Formation of the lipid coating on the finely divided substrate results in a high volume efficiency of the vesicle preparation and allows for large-scale batches to be produced in ordinary laboratory apparatus. The lipid-coated particles are introduced into an aqueous hydrating medium. The accompanying swelling of the particles fragments the liquid layer, thereby separating it from the particle surface. Fragments of the lipid dispersed in the hydrating medium are themodynamically unstable and inherently tend to form into vesicles which encapsulate a portion of the hydrating medium.

Preferably, to form the lipid coating, the dry water-swellable particles are added to a solution of lipids in an organic solvent. Optionally, additional components, e.g., drugs, lipid conjugates or conjugate precursors, etc., to be incorporated into the membrane of the vesicles are added to the organic solvent. The organic solvent is evaporated to deposit the lipids and any additional components as a composite coating or film on the surfaces of the particles.

When the coated water-swellable particles are combined with the aqueous hydrating medium, such as an aqueous buffer solution, the particles rapidly swell and "burst", so as to fragment the lipid coating thereon. The fragmenting of the lipid coating occurs extremely rapidly. The fragments of the lipid coating are separated from the surface, so as to be completely surrounded by the hydrating medium and tend to form vesicles. Accordingly, the hydration process is much accelerated, as hydration is not "unidirectional" or limited to a single surface, for example, as in the prior art film-formation technique described above. In such prior art technique, the hydrating process, in effect, peels successive layers of the lipid coating adhering to the surface, each coating being exposed, in turn, to the hydrating medium. The hydrating process of the present invention is not so limited. Rather, the hydrating process is multidirectional, in that hydration occurs concurrently at several surfaces of the lipid fragments. Such multidirection hydration accelerates separation of the individual layers of the fragments which, in turn, form vesicles. The vesicles so formed are recovered from the hydrating phase and may be subjected to purification and sizing.

Accordingly, the present invention contemplates initially forming a lipid coating or film, which may contain other components, on a deformable surface. The lipid coating is exposed to a hydrating medium while the surface is deformed, so as to stress and thereby induce fractures in such coating. As a result, the coating is caused to fragment and separate from the surface. The fragments of the lipid coating, being no longer restricted on the surface, are subjected to multi-directional hydration, whereby the individual lipid layers of such fragments are rapidly separated. These fragmented lipid layers tend naturally to form vesicles, since they are thermodynamically unstable in "unclosed" form, the "closed" or vesicle form of a lipid layer being the more stable thermodynamic state.

The fragmentation and separation of the lipid coating is facilitated by proper choice of the characteristics of the surface upon which lipid deposition is to be made. During lipid deposition, the surface preferably should be sufficiently hydrophobic, so as to be compatible with the deposited lipid coating. During hydration and fragmentation, however, such surface preferably should exhibit hydrophilic properties so as to reject such lipid coating fragments. Preferably, materials which swell in an aqueous medium are used, since such materials will generally exhibit hydrophilic properties when hydrated. Such characteristics are not critical, since vesicle formation is accelerated by any technique whereby pieces or fragments of the lipid coating are removed from the surface and subjected to multidirectional hydration.

DESCRIPTION OF THE PREFERRED EMBODIMENTS

Preferred embodiments of the present invention for forming vesicles contemplate the use of a deformable surface, e.g., of a water-swellable particle, as a substrate upon which a lipid coating is deposited. Such deposition is made from a liquid phase, e.g., by evaporation. The lipid coating may include other components to be incorporated in the membrane of the vesicles to be formed. Preferably, the substrate surface is sufficiently hydrophobic, when dry, to be compatible with the lipid coating during deposition. Also, the substrate surface, when hydrated, preferably exhibits a hydrophilic property with respect to the lipid coating. Accordingly, fragmenting of the lipid layer upon deformation of the substrate surface, e.g., swelling of the particles, during the hydrating process and also the accompanying change in the character of the surface accelerates release of lipid fragments from such surface and formation of vesicles in the hydrating medium.

As used herein, the term "vesicle" refers to a synthetic cell-like structure that comprises a membrane composed of lipids or lipid-like materials and having at least one or more aqueous compartments surrounded by such membrane.

The term "lipid" refers to any substance that comprises long, fatty-acid chains, preferably of 10-20 carbon units. The term "lipid-like" refers to substances having hydrophobic moieties of similar physical or chemical natures as lipids, e.g., molecules having polyhalocarbon chains. Lipids or lipid-like materials used to form vesicles have a polar group at one end of the molecule and a hydrophobic moiety at the end. Such materials, also called "amphiphiles" are, for example, phosphatidyl cholines, phosphatidyl ethanolamines, phosphatidyl serines, sphingomyelins, cardiolipins, plasmalogens and cerebrosides.

Also, other materials may be combined with the lipids, such as fillers and liquefiers in forming the membrane. Cholesterol and other sterols or compounds having similar structure and physical properties can be used for such purposes. The amount of filler and/or liquefier can be varied, as known in the art, to achieve a desired stability and permeability of the vesicles.

Also, and as known in the art, materials may be used with lipids, e.g., polyfluorinated hydrocarbons, to deliberately disrupt continuity of the membrane by forming separate phases, and thereby modify the membrane permeability and control the release of the encapsulated material, as necessary, for diagnostic or therapeutic purposes. In addition, polymerizable monomers can be added to the membrane formulation. After formation of the membrane, these monomers are polymerized using chemical or physical techniques, to cross-link the membrane, thereby rendering it mechanically stronger and less permeable. Monomers that are reversibly depolymerizable may be added to the membrane formulation and polymerized, to improve storage stability. Upon depolymerization, the original properties of the membrane are restored.

Another class of materials suitable for forming vesicles are electrically charged lipids or other amphiphiles, which induce a net charge into the membrane. As a result, the vesicles tend to remain separated in solution due to electrostatic repulsion. Accordingly, such vesicles tend not to aggregate and remain dispersed within a liquid sample medium, so as to facilitate reaction with other solutes present therein.

Also, chemical stabilizers are often used in membrane formulations. For example, antioxidants, e.g., alpha-tocopherol, are often used to prevent oxidation of double bonds found in certain lipids. Oxidation of such double bonds can result in undesirable changes in the chemical and physical properties of the membrane.

Generally, in use, reagents are intimately associated with the vesicles, either being encapsulated therein or incorporated in the membrane proper and render such vesicles suitable for diagnostic or therapeutic purposes. Whether the reagent is encapsulated within a vesicle or incorporated in its membrane is determined by the intended use of such vesicle and the properties of the such reagent. For diagnostic purposes, for example, as in a liposome-based immunoassay, a reagent such as an enzyme is encapsulated in the vesicle and, also, antigen is conjugated to or exposed from the exterior surface of its membrane. Reference is made to Francis X. Cole, U.S. Pat. No. 4,342,826 and R. H. Adolfsen et al U.S. Ser. No. 678,531, filed on Dec. 5, 1984 and assigned to the same assignee. The analyte in a sample volume competes with such antigen for a limited amount of antibody. When an antigen/antibody complex is formed on the vesicle, in the presence of a lysing reagent, e.g., complement, immunolysis occurs and the encapsulated reagent can thereby to react with a component (substrate) present in or introduced into the sample medium. The amount of immunolysis, as indicated by the quantity of reagent reacted, provides an indication of analyte concentration. Typically, lipid-antigen conjugates are cholesterol-based or phosphatidyl ethanolamine-based. A conjugate need not be present in the membrane formation. Alternatively, for example, a conjugate precursor can be present in the membrane formulation and used as an anchor for conjugation after vesicle formation by known technique. Reference is made to Heath et al, Biochim. Biophys. Acta 640, 66 (1981) Also, marker materials, such as spin labels, radioisotope-labelled compounds, etc. can be encapsulated in the vesicle to indicate the amount of immunolysis, or sample concentration.

For therapeutic purposes, water-soluble drugs can be encapsulated in vesicles, or water-insoluble drugs may be incorporated in the membrane of a vesicle. The vesicle is targeted to a particular organ in a patient, whereby such vesicle is used as a vehicle for delivering such drug to the organ. If water-insoluble materials are to be encapsulated, organic co-solvents miscible with water may be added to the hydrating mixture to solubilize the same. The amount of co-solvents added should not adversely affect the stability of the vesicles. Other components that may be added to the hydrating mixtures are buffers to maintain constant pH and ionic strengths during vesicle formation and also stabilizers, such as agents to prevent bacterial growth in the hydrating mixture, co-factors needed for maintaining enzyme reactivity and antioxidants.

The particles of water-swellable material upon which the liquid film is deposited preferably have a smooth surface, a size between 10 and 1000 microns, and a narrow size distribution. The surface should exhibit sufficient hydrophobicity when dry to be compatible with the deposited lipid coating and exhibit hydrophilicity when hydrated. Accordingly, dry particles should be dispersed and not aggregate when introduced into the organic solvent containing lipids and that the lipid coating should adhere to the surfaces of such particles. However, in presence of an aqueous medium, the particles tend to be hydrated by the polar environment and reject such a lipid layer. Materials having such properties are organic polymers, such as polyamides or polysaccharides, and inorganic polymers, such as silica or zeolites.

Also, such particles should exhibit a sufficient degree of swelling upon hydration to fragment the lipid coating thereon. The degree of swelling is determined by the three-dimensional structure of the material forming the particle and varies inversely as the degree of cross-linking of such structure. Also, swelling depends upon the chemical nature of the material, very polar and hydrophilic functionalities tending to enhance swelling. Hence, the preferred particles of the invention have a large proportion of such functionalities in their structure. On the other hand, such particles are sufficiently cross-linked, such that only water and buffer salts present in the hydrating medium penetrate into the particles and large molecular weight materials to be encapsulated within the vesicles, e.g., proteins, nucleic acids, etc., are excluded during hydration. Hence, due to the rapid swelling of the particles, the large molecular weight materials to be encapsulated tend to become concentrated at the interface between the lipid coating and the surrounding hydration medium, whereby the efficiency of encapsulation during vesicle formation is enhanced. The use of particles rather than a continuous surface allows for a high volume efficiency during the vesicle formation process.

Accordingly, the method of forming liposomes according to the invention comprises, at least, two distinct steps, i.e., the formation of the lipid coating onto the deformable surface (or water-swellable particle), and the deformation of such surface during hydration to separate the deposited lipid coating, whereby the separated lipid coating is subjected to multi-directional hydration and vesicle formation is accelerated.

Lipid or lipid-like mixtures for defining the membranes of the vesicles are initially dissolved in a suitable organic solvent, which is chemically compatible with the particles. The dry, water-swellable particles are then added to the organic solution. The organic solution is rotated or shaken to to thoroughly mix the particle suspension. The organic solvent is then evaporated, whereby the remaining lipid or lipid-like material forms a coating on the surfaces of the particles. Other methods of forming a lipid coating of the particles are available. For example, particles can be introduced into a lipid mixture which is maintained above its phase-transition temperature, so as to be in a fluid state. Accordingly, constant rotating or shaking of such mixture results in a thin lipid coating being formed on the particles. Care should be exercised not to elevate the temperature excessively, so as to avoid any chemical changes in the materials involved or any physical deterioration of the particles. If desired, sonication may be employed during the mixing process, to insure an even lipid coating on the surfaces of the particles. Accordingly, the invention contemplates any technique whereby lipids or lipid-like mixtures can be deposited as a coating on the surface of a deformable substrate or water-swellable particles.

Hydration is effected by introducing the lipid-coated particles into an aqueous solution of materials to be encapsulated within the vesicle to be formed. Hydration can be accelerated or decelerated by an appropriate choice of temperature, which preferably is above the phase-transition temperature of the lipid coating.

The separation and purification process, whereby solids in the hydrating mixture and vesicles are separated, is preferably achieved by filtration. The hydrating mixture, containing the vesicles, is passed through a filter whose pores allow only vesicles to pass and not the now-swollen particles. Other known methods of separation can involve precipitation or, conversely, flotation of the vesicles and particle chromatography. Accordingly, the present invention contemplates the use of any technique whereby the vesicles can be separated.

If desired, size homogenization of the vesicles can be performed at this stage by the known techniques of "extruding" the suspension through a membrane having smooth, uniform pores of desired diameter. When passed through such pores, larger vesicles are reformed into smaller vesicles of controlled size.

The process of purification of the vesicles may be achieved by a series of controlled speed centrifugations, as known in the art. The suspension of vesicles is centrifuged and supernatant is decanted. The separated vesicles are then washed and resuspended in buffer. The resulting suspension is centrifuged and the process repeated until sufficient purification is achieved. Alternatively, purification can be effected by known column chromatography techniques. Accordingly, the present invention contemplates the use of any suitable prior art process for purifying vesicles.

In the following working Examples, wherein standard commercially available chemicals were used wherever possible, illustrate preferred methods for forming lipid vesicles according to the present invention. All chemicals mentioned were purchased from Sigma Chemicals Company, St. Louis, Mo.

EXAMPLE I

This example describes a preparation of vesicles according to the method of the invention, whereby the vesicles contain beta-galactosidase and are sensitized with a thyroxine-modified phospholipid for use in a non-isotopic immunoassay for thyroxine.

A mixture of 22 mg phosphatidyl choline (PC), 5.25 mg dicetyl phosphate (DCP), 8.7 mg cholesterol, 0.65 mg alpha tocopherol and 2.2 mg thyroxine-dinitrophenyl phosphatidyl ethanolamine in 40 ml chloroform was evaporated to dryness onto 1.5 gr polyacrylamide beads, (Biorad p-2, −400 mesh) in a 100 ml boiling flask evacuated at 40° C. for one hour using a water aspirator, and subsequently a vacuum pump at 0.9 Torr. for one hour at ambient temperature. The lipid-coated beads were cooled to 4° C. and hydrated by addition of a solution of 29 mg (15,000 units) beta-galactosidase (Grade VIII), dissolved in 10.5 ml barbital buffer, pH 8.5 (0.05 M barbital, 0.1 M NaCl). An immediate swelling of the beads and removal of the lipid coating thereon occurred immediately. The vesicle formed at a very fast rate and the system was observed visually to stabilize within a few seconds. After shaking the contents of the flask for a few minutes, the swollen polyacrylamide beads were filtered through a medium-sized sintered glass filter (10–15 micron pore size, while applying pressure. The filtrate was subjected to four centrifugation/wash cycles, the centrifugation being at speeds of 15,000, 20,000, 20,000 and 20,000 rpm, respectively, for 30 minutes in an L8-55 ultracentifuge (Beckman Instruments Inc. Palo Alto, Calif.) 8° C. and using 70 ml polycarbonate tube. The pellet of vesicles was recovered and washed, using 15 ml barbital buffer. Material sticking to the tube wall after the last wash consisted of lipids that did not form vesicles and was discarded. The final pellet was resuspended in 6 ml buffer for a total volume of about 6.5 ml. The vesicles were assayed for beta-galactosidase activity by addition of 30 $\mu$l of a vesicle suspension diluted 1:40 in tris-(hydroxymethyl) amine (TRIS) buffer, pH 7.5 (0.05 TRIS, 0.15 M. NaCl, 0.1% sodium azide) to two glass tubes containing 270 $\mu$l of a solution containing 60 mg % of o-nitrophenyl-beta-galactopyranoside and 0.001 M magnesium chloride. One of the glass tubes contained 0.1% Triton X-100 in TRIS buffer and served as the lysing agent. The color developed in each glass tube was monitored at 405 nm. Vesicles lysed by 0.1% Triton X-100 gave a rate value of 365 whereas non-lysed ones had a rate value of 11.5 mA/min. The vesicles were immunoreactive in a thyroxine assay protocol, and the amount of material thus made was sufficient for about 20,000 assays. The example illustrates that vesicles made by the method of the invention efficiently encapsulated the hydrating medium and are suitable for use in liposome immunoassays.

EXAMPLE II

A mixture of 11 mg phosphatidyl choline, 2.6 mg dicetyl phosphate and 4.5 mg of cholestanol in 5 ml of chloroform was evaporated onto 1 gr polyacrylamide particles in a 25-ml roundbottom flask, as in Example I. After evacuation of 0.9 Torr. for 0.5 hour at room temperature, the flask was cooled to 4° C. The lipid-coated particles were hydrated with a solution of 7 ml TRIS buffer, pH 7.5 (0.05 M TRIS, 0.150 M NaCl) in which 35 mg of horseradish peroxidase Type I was dissolved, which was precooled to 4° C. Again, vesicles formed instantly. The resulting mixture was filtered through a 10-micron filter, using pressure. The resulting vesicle suspension was centrifuged, as in Example I, to separate the vesicles from unentrapped enzyme. The final volume of vesicle prepartion was adjusted to 4 ml. 30 $\mu$l of a 1:400 dilution of the vesicle preparation in the same TRIS buffer was added separately to two optical cuvettes, one containing 120 μl of TRIS buffer and the other containing 120 μl TRIS buffer in which TRITON X-100 at a concentration of 2% was present. Each cuvette was incubated for 5 minutes at 37° C. then, to each cuvette 50 μl of 0.1 M sodium 3-(N-Ethyl anilino) propyl sulfonate, 100 μl of 0.2 M 4-aminoantipyrene and 50 μl of 0.01% hydrogen peroxide (all in TRIS buffer) were added, and the rate of color formation read at 500 nm at 37°. The vesicles lysed by the surfactant gave a rate value of 135 mA/min. The non-lysed vesicles gave a rate value of 29 mA/min.

EXAMPLE III

Example II was repeated on a a 10-fold scale, using a 250 ml round-bottom flask. The volume of the resulting vesicle suspension was adjusted to 40 ml. The vesicles were assayed for enzymatic activity with and without lysis by TRITON X-100, as in Example II. Lysed vesicles gave a rate value of 138 mA/min. Non-lysed vesicles gave a rate value of 25 mA/min. For normal use in immunoassays, such a preparation would be sufficient for half of million tests and, yet, is easily prepared in ordinary laboratory apparatus.

It should be understood by those skilled in the art that various modifications may be made in the present invention without departing from the spirit and scope thereof as described in the specification and defined in the appended claims.

What is claimed is:

1. A method of preparing vesicles, which method comprises:
   a. depositing a coating of lipid onto the surface of one or more particles, said particles being deformable in a hydrating aqueous phase, to form a coated particle; and
   b. deforming said coated particle by contacting it with a hydrating aqueous phase in order to fragment said lipid coating so as to disperse fragments of said lipid into said aqueous phase and subject said fragments to multidirectional hydration, whereby lipid vesicles are formed in said aqueous phase.

2. The method of claim 1, wherein said depositing step comprises forming an organic phase comprising lipid and an organic solvent, contacting said deformable particle with said organic phase, and evaporating said organic solvent, said deformable particle being formed of a material which is sufficiently hydrophobic when exposed to said organic phase to permit deposition of said lipid coating.

3. The method of claim 1, wherein said depositing step comprises forming an organic phase comprising lipids in a fluid state, and contacting said deformable particle with said organic phase.

4. The method of claim 2 or 3, comprising the additional step of separating said coated particles from components of said organic phase which have not coated said particle.

5. The method of claim 2 or 3, wherein said organic phase comprises a phospholipid.

6. The method of claim 2 or 3, wherein said organic phase further comprises cholesterol.

7. The method of claim 2 or 3, wherein said organic phase further comprises cholestanol.

8. The method of claim 2 or 3, wherein said organic phase further comprises a ligand-lipid conjugate.

9. The method of claim 2 or 3, wherein said organic phase further comprises at least one therapeutically effective substance.

10. The method of claim 1, further comprising the step of introducing a marker into said aqueous phase prior to contacting said aqueous phase with said coated particle, said marker being selected from the group consisting of enzymes, substrates, fluorphors, spin-label markers, luminophors and radioisotopes.

11. The method of claim 1, further comprising the step of introducing a therapeutically effective drug into said aqueous phase prior to contacting with said coated particle.

12. The method of claim 1, wherein said deformable particle is formed of a material which swells when exposed to said aqueous phase.

13. The method of claim 1, wherein said depositing step comprises depositing said lipid coating onto the surface of one or more water-swellable particles.

14. The method of claim 13, wherein said depositing step comprises depositing said lipid coating onto the surface of one or more polymeric particles.

15. The method of claim 14, wherein said depositing step comprises depositing said lipid coating onto the surface of one or more particles formed of a material selected from the group consisting of polyamides, and polysaccharides.

* * * * *